United States Patent
Gubelmann-Bonneau et al.

(10) Patent No.: US 6,455,471 B1
(45) Date of Patent: Sep. 24, 2002

(54) PESTICIDAL COMPOSITIONS

(75) Inventors: Isabelle Gubelmann-Bonneau, Princeton, NJ (US); Freddy Pfammatter, Collonges (CH); Christian Schlatter, Greensboro, NC (US); Manfred Vogt, Bad Säckingen (DE)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 09/601,945

(22) PCT Filed: Feb. 8, 1999

(86) PCT No.: PCT/EP99/00818

§ 371 (c)(1),
(2), (4) Date: Oct. 4, 2000

(87) PCT Pub. No.: WO99/40784

PCT Pub. Date: Aug. 19, 1999

(30) Foreign Application Priority Data

Feb. 10, 1998 (EP) .............................................. 98810098

(51) Int. Cl.[7] .............................................. A01N 43/64
(52) U.S. Cl. ...................................... 504/133; 504/134
(58) Field of Search .................................. 504/133, 134

(56) References Cited

U.S. PATENT DOCUMENTS

| 4,461,641 A |   | 7/1984  | Abildt et al. |
|-------------|---|---------|---------------|
| 4,770,694 A |   | 9/1988  | Tesuji et al. |
| 4,814,000 A | * | 3/1989  | Ciocca et al. ............... 71/111 |
| 5,074,905 A |   | 12/1991 | Frisch et al. |
| 5,518,991 A | * | 5/1996  | Frisch et al. ............. 504/138 |

FOREIGN PATENT DOCUMENTS

| CA | 2031322    |   | 6/1991  |
| CA | 2127485    |   | 1/1995  |
| EP | 0 088 049  |   | 9/1983  |
| EP | 0 261 492  |   | 3/1988  |
| EP | 0 432 062  |   | 6/1991  |
| EP | 0 514 769  |   | 11/1992 |
| EP | 0 633 057  |   | 1/1995  |
| WO | 9637101    | * | 11/1996 |
| WO | WO96/37101 |   | 11/1996 |
| WO | WO 96/37101 |  | 11/1996 |

OTHER PUBLICATIONS

Derwent WPI database abstract, 010137055 for EP 633057, Compsn. contg. phosphated poly–alkoxylated tristyryl–phenol deriv.—and glycerol, used as stabiliser for active ingredient in agrochemical compsn. 1995, V. Bramati and A. Marchetto.

Derwent WPI database abstract, 008669276 for EP 432062, Conc. micro–emulsions of water–insol. organic cpds.—esp. phytosanitary product, comprises water–insol. organic cpds. in mixed surfactant system. 1991, J F Fiard and C>malavieill.

* cited by examiner

*Primary Examiner*—Alton Pryor
(74) *Attorney, Agent, or Firm*—William A. Teoli, Jr.; Rose M. Allen

(57) ABSTRACT

A pesticidal composition in the form of an aqueous suspoemulsion, comprising at least two pesticides A and B which are substantially insoluble in water, wherein pesticide A is solid and pesticide B is liquid or dissolved in a hydrophobic organic solvent, and a combination of surfactants comprising (1) a tristyrylphenol-ethoxylate having 6–14, in nonionic form and (2) a tristyrylphenol-ethoxylate having 14–18 mol ethoxylate, in form of its sulfate or phosphate, in anionic or acid form, and (3) a dioctyl-sulfosuccinate salt.

10 Claims, No Drawings

PESTICIDAL COMPOSITIONS

This application is a 371 of PCT/EP99/00818 filed Feb. 8, 1999.

The present invention relates to pesticidal compositions in form of aqueous suspoemulsions, comprising at least two pesticides which are substantially insoluble in water, wherein one pesticide A is solid and the other pesticide B is liquid or is dissolved in a hydrophobic organic solvent, and a combination of surfactants comprising (1) a tristyrylphenol-ethoxylate having 6–14 mol ethoxylate, in nonionic form, and
(2) a tristyrylphenol-ethoxylate having 14–18 mol ethoxylate in form of its sulfate or phosphate, in anionic or acid form, and
(3) a dialkyl-sulfosuccinate salt.

Suspoemulsions according to the invention consist of at least three phases: an aqueous phase, comprising pesticide A in solid dispersed form, and an organic phase comprising pesticide B, either in liquid form or dissolved in an organic hydrophobic solvent. Normally the aqueous phase is the continuous phase. Such suspoemulsions are very sensible systems regarding physical and chemical stability.

Suspoemulsions comprising pesticides are described for example in EP 88,049, EP 143,099 and EP 261,492.

However, the known suspoemulsions do not always satisfy the needs of agricultural practice in many incidents and aspects: some suspoemulsions are not suitable for certain pesticide combination due to lacking stability. For example, they become inhomogeneous on storage, pH or viscosity are not remaining constant, particle size is growing which may plug the nozzle of the spray device, or the active ingredient may decompose. As a result the handling is rendered difficult and the biological efficacy is reduced. Furtheron, some of the surfactants used in the known suspoemulsions, as alkylphenol ethoxylates, for example nonylphenol ethoxylates, are not entirely satisfactory with respect to their ecological and toxicological properties, and their replacement is desirable.

The suspoemulsions provided herewith are storage stable, easy to apply, ecological and toxicological favourable and have good pesticidal efficacy. The compositions according to the invention are stable for at least 12 months at 25° C.

Suitable salts of the surfactants are, for example, metal salts, such as alkali metal or alkaline earth metal salts, for example sodium, potassium calcium or magnesium salts, or salts with ammonia or an organic amine, such as morpholine, piperidine, pyrrolidine, a mono-, di- or tri-lower alkylamine, for example ethyl-, diethyl-, triethyl- or dimethyl-propylamine, or a mono-, di- or tri-hydroxy-lower alkylamine, for example mono-, di- or tri-ethanolamine. Preferred combinations of surfactants are (1) a tristyrylphenol-ethoxylate having 8–12, preferably 10 mol ethoxylate, and
(2) a tristyrylphenol-ethoxylate having 16 mol ethoxylate, in form of its sulfate or phosphate, preferably in form of its ammonuim sulfate, and
(3) a dioctyl-sulfosuccinate salt, preferably the sodium salt.

Pesticides which are substantially insoluble in water means their solubility at room temperature is less than 2%, preferably less than 0.2%. Liquid means the melting point is below 30° C.

The term pesticide is understood to encompass herbicides, insecticides, acaricides, nematicides, ectoparasiticides, fungicides and plant growth regulators; many of them are described in The Pesticide Manual, 11th Ed, British Crop Protection Council. Preference is given to herbicides.

Suitable herbicides A, which are solid and substantially insoluble water are for example triazine derivatives, as atrazine, terbutryn, prometryn, terbuthylazine, ametryn, cyanazine, desmetrine, propazine, simazine, simetryn, terbumeton; preferred ar atrazine, terbutryn, prometryn, and terbuthylazine; or urea derivatives, as isoproturon, chlorobromuron, chlorotoluron, diuron, metobromuron, metoxuron. Suitable herbicides B, which are liquid or soluble in a hydrophobic organic solvent, are acetanilide derivatives, as alachlor, metolachlor or S-metolachlor (S-enantiomer of racemic metolachlor); preferred are metolachlor and S-metolachlor. Particularly preferred are the combinations atrazine|metolachlor and atrazine/S-metolachlor. It may be advantageous to combine the herbicides with a safener, for example with benoxacor.

Suitable fungicides A are for example sulfur, copperhydroxide, mancozeb, folpet, chlorthalonil, carbendazim, acibenzolar-S-methyl. Suitable fungicides B are for example benomyl, cyprodinil, dimethomorph, edifenphos, fenpropimorph, metalaxyl, (R)-metalaxyl (enantiomer), oxadixyl, pyrifenox, thiabendazol, tridemorph, azoxystrobin, kresoxim-methyl or triazoles such as propiconazol, difenoconazol, bromoconazol, cyproconazole, epoxyconazol, hexaconazol, ipconazol, fenbuconazol, myclobutanil, penconazol, tebuconazol, triadimefon, triadimenol, tetraconazol, triticonazol, or uniconazol; furtheron famoxadone, quinoxyfen, spiroxamin, fludioxonil, fenpiclonil, fenhexamid and 2-[α-{[(α-methyl-3-trifluoromethyl-benzyl)imino]-oxy}-o-tolyl] -glyoxylic acid-methylester-O-methyloxim.

Suitable insecticides/acaricides are benthiocarb, diflubenzuron, teflubenzuron, lufenuron, diafenthiuron or pyrethroide such as bifenthrin, bioallethrin, tau-fluvalinate, resmethrin, permethrin, cypermethrin, cyfluthrin, cyhalothrin, deltamethrin, tefluthrin or tetramethrin; furtheron pymetrozin, thiocyclam, fenoxycarb, methopren, abamectin and emamectin.

Suitable hydrophobic organic solvents in which the pesticides may be dissolved are aliphatic and aromatic hydrocarbons such as hexane, cyclohexane, benzene, toluene, xylene, mineral oil or kerosin, mixtures or substituted naphthalenes, mixtures of mono- and polyalkylated aromatics, halogenated hydroarbons such as methylene chloride, chloroform and o-dichlorobenzene; phthalates, such as dibutyl phthalate or dioctyl phthalate; ethers and esters, such as ethylene glycol monomethyl or monoethyl ether, fatty acid esters; pyrrolinones, such as N-octylpyrrolidone, ketones, such as cyclohexanone; plant oils such as castor oil, soybean oil, cottonseed oil and possible methyl esters thereof; as well as epoxidised coconut oil or soybean oil.

The amount of organic solvent is not critical and can vary from 0 to 50%, depending on the solubility of the respective pesticide.

The average size of the suspended particles is 0.5 to 20, preferably 1 to 5 microns when measured with a laser particle analyzer, e.g a CILAS 920 apparatus.

The viscosity of the suspoemulsion is 100 to 2000, preferably 200 to 1500, most preferably 300 to 1000 mPas when measured with a BROOKFIELD viscosymeter with spindle 3 at 30 rpm and 20° C.

Suitable concentrations in relation to the composition are (% weight/weight): 1 to 95%, preferably 5 to 90%, more preferably 10 to 80% by weight of pesticides A and B, 3 to 90%, preferably 5 to 80%, more preferably 10 to 60% by weight of water, and 1 to 40%, preferably 2 to 20%, more preferably 4 to 12%, most preferably 6–8% by weight of the surfactants (1), (2) and (3) in total.

The ratio of the pesticide A: pesticide B is 1:99 to 99:1, preferably 1:5 to 5:1 and 1:2 to 2:1. The concentration of the surfactants is

- 0.5 to 20%, preferably 1 to 10%, more preferably 1 to 5% by weight of surfactant (1)
- 0.2 to 15%, preferably 0.5 to 10%, more preferably 1 to 5% by weight of surfactant (2)
- 0.2 to 20%, preferably 0.5 to 15%, more preferably 1 to 5% by weight of surfactant (3).

The composition according to the invention may comprise additional dispersants and adjuvants, as (in % by weight)

a dispersing agent, 0 to 20%, preferably 0.2 to 5%, e.g. fatty alcohole ethers, fatty acid esters, arylsultonates as polynaphtalensulfonate, alkylarylsulfonates as dodecylbenzene sulfonate, alkylsulfonates as sodium sulfosuccinate, polyalkyleneglycol ethers, acrylic Graft Co-Polymer, N-methly-N-oleyl-taurin Na salt or polyvinylalkohol, preferably 0.2 to 5% dodecylbenzene sulfonate calcium;

a thickening agent, 0 to 2%, preferably 0.1 to 1%, e.g. xanthan gum, heteropolysaccharides, oxypropylated cellulose, precipitated or fused silica (hydrophobizised or non-hydrophobizised), gelatine, polysaccharides, tetramethyl decyne diol, ethoxylated dialkyl phenol, methylated clay, propylene carbonate, hydrogenated castor oil, ethoxylated vegetable oil, sodium benzoate or hexanediol;

an antifreeze agent, 0 to 20%, preferably 1 to 10%, e.g. 1,2-propyleneglycol, glycerine, ethyleneglycol or freezing point-lowering salts;

a defoaming agent, 0 to 5%, preferably 0.1 to 2%, e.g. silicone oil, alcohols, fluoroorganics or mineral oils;

a preservative/biocide, 0 to 10%, preferably 0.1 to 3%, e.g. formaldehyde, 1,2 benzisothiazol-3(2H)-one or its salts, or benzoic acid;

a buffer, 0 to 5%, preferably 0.1 to 3%, e.g. acetic acid (AcOH)/NaOH or AcOH/KOH, $H_3PO_4$/NaOH or $H_3PO_4$/KOH, citric acid/NaOH or citric acid/KOH, or $KH_2PO_4$/Borax; as well as further wetting, dispersing and emulsifying agents, organic solvents, cosolvents and oils.

Another object of the invention is a process for preparing a composition as herein described, by grinding or milling the solid pesticide and then intimateley mixing, optionally by warming, the components, until a homogeneous phase is achieved.

In another aspect of the invention the composition is an aqueous spray mixture. Before the application, the composition of the invention may be diluted with water by simple mixing at ambient temperature in order to get a ready for use spray mixture.

The resulting spray mixtures are stable, i.e. they remain as a homogeneously dispersed phase on standing without agitation for at least one hour to 12 hours or even more. Preferred concentrations of the spray mixture are 0.05 to 10%, more preferred 0.2 to 5% pesticide in relation to the spray mixture.

A further aspect of the invention is a method of preventing or combatting undesirable plant growth, infestation of plants or animals by pests and regulating plant growth by diluting the composition according to claim 1 with water and applying a pesticidally effective amount to the cultivation area, to the plant or animal.

PREPARATION EXAMPLES

The following Examples illustrate the invention in more detail. The registered trademarks and other designations denote the following products: The suppliers are known or may easily be found, e.g. in "McCutcheon's Emulsifiers and Detergents", Rock Road, Glen Rock, N.J. 07452-1700, USA, 1997.

| | | |
|---|---|---|
| SOPROPHOR TS 10 ® | Tristyrylphenol-10 EO | surfactant (1) |
| SOPROPHOR TS 8 ® (supplier: RHODIA, 25, Quai Paul Doumer F-92408 Courbevoie) | Tristyrylphenol-8 EO | |
| SOPROPHOR 4 D 384 ® (RHODIA) | Tristyrylphenol-16 EO, ammonium sulfate | surfactant (2) |
| GEROPON DOS/PG ® (RHODIA) | sodium dioctyl sulfosuccinate (65% in propyleneglycol) | surfactant (3) |
| ANTIFOAM A (DOW) RHODORSIL 426 and 454 (RHODIA) | polymethylsiloxan | defoaming agent |
| PROXEL GXL (ICI) PROXEL BD (ICI) | sodium 1,2 benzisothiazol-3(2H)-one, 1,2 benzisothiazol-3(2H)-one | preservative/ biocide |
| RHODOPOL 23 (RHODIA) | heteropolysaccharides | thickener |
| ATLOX 4913 (ICI) | Acryl Craft Copolymer (in water/PG) | dispersing agent |

EO = ethyleneoxid

The components are intimately mixed, optionally by warming, until a homogeneous phase is achieved.

All the compositions according to the examples are stable for at least 12 months at 25° C. After diluting with water the compositions form ready to use spray mixtures. The numbers given in the Examples are concentrations in % weigh/weight.

EXAMPLES 1

| | | 1a | 1b | 1c | 1d |
|---|---|---|---|---|---|
| herbicide A | Atrazine | 17 | 31 | 31 | 31 |
| herbicide B | Metolachlor | 33 | 21 | 21 | 21 |
| surfactant (1) | Soprophor TS 10 | 4.6 | 4.6 | 1.5 | 2.5 |
| surfactant (2) | Soprophor 4D384 | 1.2 | 1.2 | 2 | 2.5 |
| surfactant (3) | Geropon DOS/PG | 1.2 | 1.2 | 4 | 3 |
| antifreezer | 1,2 Propylenglycol | 5 | 5 | 5 | 2 |
| defoaming agent | Rhodorsil 426 | 0.3 | 0.3 | 0.3 | 0.3 |
| preservative | Proxel BD | 0.12 | 0.12 | 0.12 | 0.12 |
| thickener | Rhodopol 23 | 0.12 | 0.12 | 0.12 | 0.12 |
| | Water | ad 100 | ad 100 | ad 100 | ad 100 |

EXAMPLES 2

|  |  | 2a | 2b | 2c | 2d | 2e | 2f |
|---|---|---|---|---|---|---|---|
| herbicide A | Atrazine | 30 | 30 | 32 | 37 | 32 | 37 |
| herbicide B | S-Metolachlor | 28.5 | 28.5 | 40 | 29 | 40 | 29 |
| surfactant (1) | Soprophor TS 10 | — | 5.4 | 4.6 | 3.8 | 4.6 | 3.8 |
| surfactant (1) | Soprophor TS 8 | 4.6 | — | — | — | — | — |
| surfactant (2) | Soprophor 4D384 | 1.2 | 1 | 1.2 | 1.4 | 1.2 | 1.4 |
| surfactant (3) | Geropon DOS/PG | 1.2 | 1.2 | 1.7 | 1.2 | 1.7 | 1.2 |
| dispersing agent | dodecylbenzene sulfonate calcium | — | — | — | — | 0.5 | 1 |
| antifreezer | 1,2 Propylenglycol | 3 | 3 | 5 | 3 | 5 | 3 |
| defoaming agent | Antifoam A | 0.3 | 0.3 | 0.3 | 0.3 | 0.3 | 0.3 |
| preservative | Proxel GXL | 0.03 | 0.03 | 0.12 | 0.03 | 0.12 | 0.03 |
| thickener | Rhodopol 23 | 0.12 | 0.12 | 0.12 | 0.12 | 0.12 | 0.12 |
|  | Water | ad 100 | ad 100 | ad 100 | ad 100 | ad 100 | ad 100 |

EXAMPLES 3

|  |  | 3a | 3b | 3c |
|---|---|---|---|---|
| herbicide A | Terbutryn | 20 | 20 | 20 |
| herbicide B | S-Metolachlor | 25 | 25 | 25 |
| surfactant (1) | Soprophor TS 10 | 4.6 | 1.5 | 2.5 |
| surfactant (2) | Soprophor 4D384 | 1.2 | 1.5 | 2 |
| surfactant (3) | Geropon DOS/PG | 1.2 | 4.5 | 3.5 |
| antifreezer | 1,2 Propylenglycol | 3 | 3 | 3 |
| defoaming agent | Antifoam A | 0.3 | 0.3 | 0.3 |
| preservative | Proxel GXL | 0.03 | 0.03 | 0.03 |
| thickener | Rhodopol 23 | 0.12 | 0.12 | 0.12 |
|  | Water | ad 100 | ad 100 | ad 100 |

EXAMPLES 4

|  |  | 4a | 4b | 4c | 4d |
|---|---|---|---|---|---|
| herbicide A | Prometryn | 20 | 20 | 20 | 20 |
| herbicide B | S-Metolachlor | 12.4 | 12.4 | 12.4 | 12.4 |
| surfactant (1) | Soprophor TS 10 | 3.8 | 4.5 | 2.5 | 4 |
| surfactant (2) | Soprophor 4D384 | 1.2 | 1.5 | 2 | 1 |
| surfactant (3) | Geropon DOS/PG | 1.2 | 1 | 2.5 | 1 |
| dispersing agent | Atlox 4913 | 2 | 2 | 2 | 2 |
| antifreezer | 1,2 Propylenglycol | 3 | 3 | 3 | 3 |
| defoaming agent | Antifoam A | 0.3 | 0.3 | 0.3 | 0.3 |
| preservative | Proxel GXL | 0.03 | 0.03 | 0.03 | 0.03 |
| thickener | Rhodopol 23 | 0.12 | 0.12 | 0.12 | 0.12 |
|  | Water | ad 100 | ad 100 | ad 100 | ad 100 |

EXAMPLES 5

|  |  | 5a | 5b | 5c |
|---|---|---|---|---|
| herbicide A | Terbuthylazin | 18.7 | 18.7 | 18.7 |
| herbicide B | S-Metolachlor | 31.3 | 31.3 | 31.3 |
| surfactant (1) | Soprophor TS 10 | 4.6 | 1.5 | 2.5 |
| surfactant (2) | Soprophor 4D384 | 1.2 | 1.2 | 2 |
| surfactant (3) | Geropon DOS/PG | 1.2 | 4.5 | 3.5 |
| dispersing agent | Atlox 4913 | 2 | 2 | 2 |
| antifreezer | 1,2 Propylenglycol | 5 | 5 | 5 |
| defoaming agent | Antifoam A | 0.2 | 0.2 | 0.2 |
| preservative | Proxel GXL | 0.03 | 0.03 | 0.03 |
| thickener | Rhodopol 23 | 0.12 | 0.12 | 0.12 |
|  | Water | ad 100 | ad 100 | ad 100 |

COMPARISON EXAMPLES

Without either of the surfactants (1), (2) and/or (3) the formulation becomes inhomogeneous after a few weeks or months at 20–25° C.

What is claimed is:

1. A pesticidal composition in the form of an aqueous suspoemulsion, comprising at least two pesticides A and B which are substantially insoluble in water, wherein pesticide A is solid and pesticide B is liquid or dissolved in a hydrophobic organic solvent, and a combination of surfactants comprising (1) a tristyrylphenol-ethoxylate having 6–14, in nonionic form and (2) a tristyrylphenol-ethoxylate having 14–18 mol ethoxylate, in form of its sulfate or phosphate, in anionic or acid form, and (3) a dioctyl-sulfosuccinate salt;

wherein said pesticide A is a triazine herbicide selected from the group consisting of atrazine, terbutryn, prometryn, and terbuthylazine; and said pesticide B is an acetanilide herbicide selected from the group consisting of metalochlor and S-metalochlor (enantiomer).

2. A composition according to claim 1, wherein the surfactants are
   (1) a tristyrylphenol-ethoxylate having 8–12 mol ethoxylate, and
   (2) a tristyrylphenol-ethoxylate having 16 mol ethoxylate, in form of its sulfate or phosphate, and
   (3) a dioctyl-sulfosuccinate salt.

3. A composition according to claim 1, comprising
   1 to 95% by weight of pesticides A and B,
   3 to 90% by weight of water,
   1 to 40% by weight of surfactants (1), (2) and (3).

4. A composition according to claim 1, wherein the ratio of the pesticide A: pesticide B is 1:99 to 99:1.

5. A composition according to claim 1, wherein the concentration of the surfactants is
   0.5 to 20% of surfactant (1),
   0.2 to 15% of surfactant (2),
   0.2 to 20% of surfactant (3).

6. A composition according to claim 1 comprising a combination selected from the group consisting of atrazine/metolachlor and atrazine/S-metolachlor.

7. A method of preventing or combatting undesirable plant growth, infestation of plants or animals by pests and regulating plant growth by diluting the composition according to claim 1 with water and applying a pesticidally effective amount to the cultivation area, to the plant or animal.

8. The composition of claim 2, wherein the tristyrylphenol-ethoxylate having 8–12mol ethoxylate has 10 mol ethoxylate.

9. The composition of claim 2, wherein the tristyrylphenol-ethoxylate having 16 mol ethoxylate, in form of its sulfate or phosphate,
   is in the form of its ammonium sulfate.

10. The composition of claim 2, wherein the dioctyl-sulfosuccinate salt is in the form of its sodium salt.

* * * * *